US010588533B2

(12) United States Patent
Sakaguchi et al.

(10) Patent No.: US 10,588,533 B2
(45) Date of Patent: Mar. 17, 2020

(54) BIOELECTRODE COMPONENT

(71) Applicant: SHINKO ELECTRIC INDUSTRIES CO., LTD., Nagano-shi, Nagano (JP)

(72) Inventors: Hideaki Sakaguchi, Nagano (JP); Yoshihiro Ihara, Nagano (JP)

(73) Assignee: SHINKO ELECTRIC INDUSTRIES CO., LTD., Nagano-Shi (JP)

(*) Notice: Subject to any disclaimer, the term of this patent is extended or adjusted under 35 U.S.C. 154(b) by 0 days.

(21) Appl. No.: 16/188,654

(22) Filed: Nov. 13, 2018

(65) Prior Publication Data
US 2019/0143091 A1 May 16, 2019

(30) Foreign Application Priority Data
Nov. 15, 2017 (JP) ................. 2017-219641

(51) Int. Cl.
A61B 5/0402 (2006.01)
A61B 5/0478 (2006.01)
A61M 37/00 (2006.01)
A61N 1/30 (2006.01)
A61B 5/0492 (2006.01)
A61B 5/0408 (2006.01)

(52) U.S. Cl.
CPC .......... A61B 5/0478 (2013.01); A61B 5/0402 (2013.01); A61B 5/0408 (2013.01); A61B 5/0492 (2013.01); A61M 37/0015 (2013.01); A61N 1/303 (2013.01); A61B 2562/0209 (2013.01); A61B 2562/125 (2013.01); A61M 2037/0053 (2013.01); A61M 2037/0061 (2013.01)

(58) Field of Classification Search
CPC .................................................. A61B 5/0478
See application file for complete search history.

(56) References Cited

U.S. PATENT DOCUMENTS

| 6,091,975 | A | * | 7/2000 | Daddona ............ A61B 5/14865 600/309 |
| 6,219,574 | B1 | | 4/2001 | Cormier et al. |
| 6,230,051 | B1 | | 5/2001 | Cormier et al. |
| 6,537,264 | B1 | | 3/2003 | Cormier et al. |
| 8,588,884 | B2 | * | 11/2013 | Hegde .................. A61B 5/0408 600/372 |
| 2002/0016562 | A1 | | 2/2002 | Cormier et al. |
| 2003/0181936 | A1 | * | 9/2003 | Trautman ............. A61B 17/205 606/186 |
| 2006/0177494 | A1 | | 8/2006 | Cormier et al. |
| 2007/0118070 | A1 | | 5/2007 | Cormier et al. |

FOREIGN PATENT DOCUMENTS

| JP | 2000-512529 | 9/2000 |
| JP | 2008-528192 | 7/2008 |

* cited by examiner

Primary Examiner — Lee S Cohen
(74) Attorney, Agent, or Firm — Rankin, Hill & Clark LLP

(57) ABSTRACT

A bioelectrode component includes an electrode member. The electrode member includes a metal plate, a coupling bar, and a needle part. The metal plate includes a first surface and a second surface opposite to the first surface, and includes an opening formed in the metal plate. The coupling bar extends inward from an inner wall of the opening. The needle part is arranged at a leading end of the coupling bar and protrudes toward the first surface of the metal plate.

19 Claims, 16 Drawing Sheets (PARTIALLY ENLARGED PERSPECTIVE VIEW)

(PARTIALLY ENLARGED PERSPECTIVE VIEW)

(PARTIALLY ENLARGED PERSPECTIVE VIEW)

(PARTIALLY ENLARGED PERSPECTIVE VIEW)

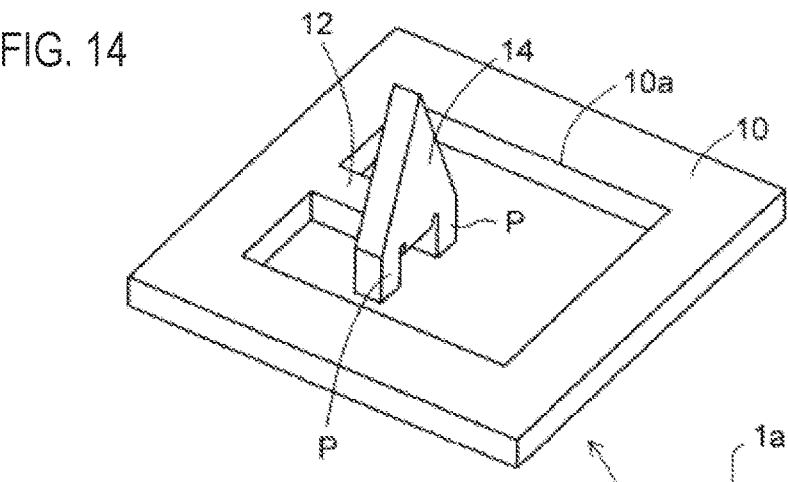
FIG. 14
(PARTIALLY ENLARGED PERSPECTIVE VIEW)
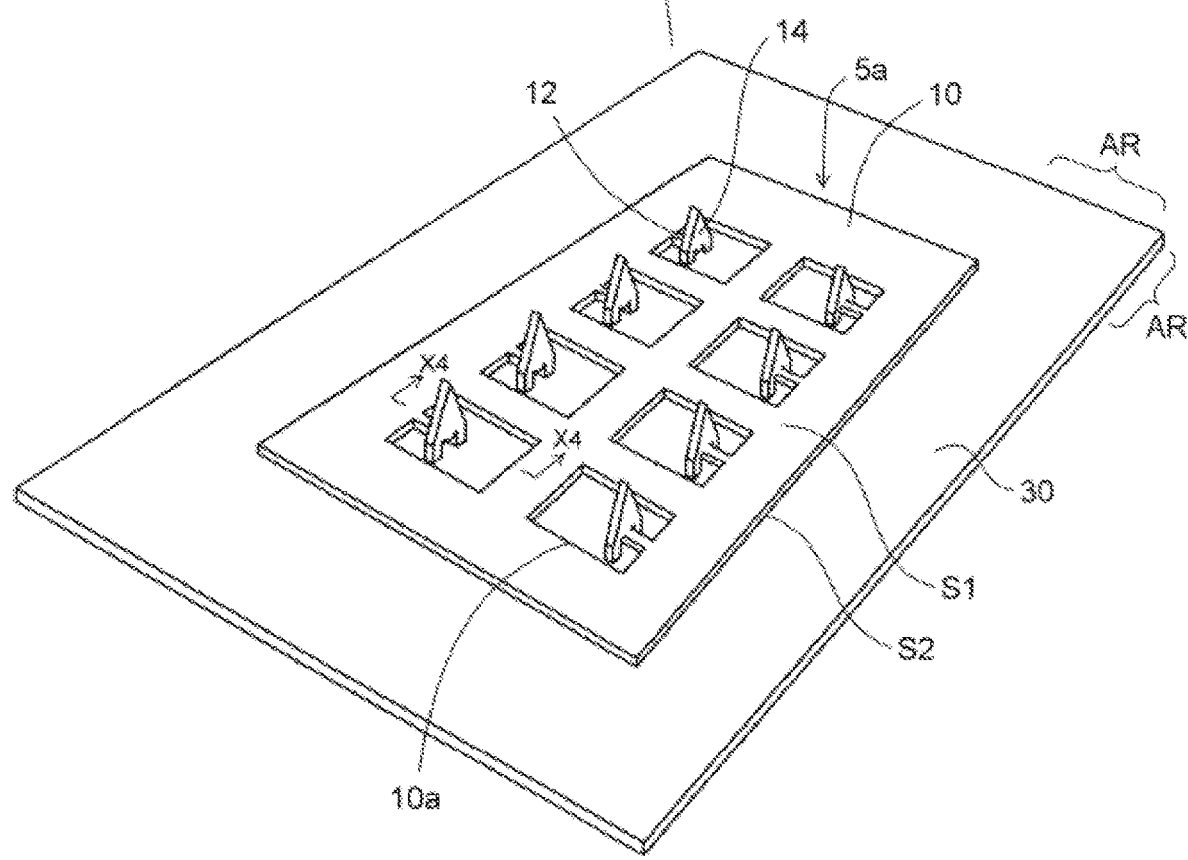

BIOELECTRODE COMPONENT

CROSS-REFERENCE TO RELATED APPLICATION

The present application claims priority from Japanese Patent Application No. 2017-219641 filed on Nov. 15, 2017, the entire content of which is incorporated herein by reference.

BACKGROUND

Technical Field

The present disclosure relates to an electrode component for a biological body (hereafter, referred to "bioelectrode component").

Related Art

In the related art, biosignals such as electrocardiogram and brain wave are measured by bringing an electrode pad into contact with skin of a human body. As the electrode pad, a pad in which particles of Ag and AgCl are mixed with a gel phase resin is used.

Also, a micro needle for hypodermic injection has been developed. In the micro needle, a plurality of small needle parts is provided on a sheet, and a layer of which skin is shallow is pierced with the needle parts, so that a medicinal agent such as vaccine is medicated into the skin and can reach an inside of the body.

Patent Document 1: JP-A-2000-512529
Patent Document 2: JP-A-2008-528192

Since the electrode pad in which the particles of Ag and AgCl are mixed with the gel phase resin is just contacted to a surface of the skin of the human body, the electrode pad is likely to be influenced due to a noise and cannot be thus applied for a utility for obtaining correct information of the human body.

Also, since the micro needle is required to be fixed to the skin of the human body for a predetermined time period by an adhesive film, the needle parts may separate from the skin by routine movement.

SUMMARY

Exemplary embodiments of the present invention provide a bioelectrode component capable of preventing a needle part of a bioelectrode component piercing a biological surface from separating from the biological surface.

A bioelectrode component according to an exemplary embodiment, comprises:
an electrode member, the electrode member comprising:
a metal plate including a first surface and a second surface opposite to the first surface and including an opening formed in the metal plate,
a coupling bar extending inward from an inner wall of the opening, and
a needle part arranged at a leading end of the coupling bar and protruding toward the first surface of the metal plate.

A manufacturing method of a bioelectrode component, the manufacturing method comprises:
processing a metal plate having a first surface and a second surface opposite to the first surface to form an opening, a coupling bar extending inward from an inner wall of the opening and a needle part coupled to the coupling bar; and
bending the needle part so as to protrude toward the first surface of the metal plate, thereby obtaining an electrode member.

According to the exemplary embodiments, the bioelectrode component includes the electrode member, the electrode member has the opening formed in the metal plate having the first surface and the second surface opposite to the first surface, and the coupling bar extends inward from the inner wall of the opening. Also, the needle part protruding toward the first surface of the metal plate is erected at the leading end of the coupling bar.

The adhesive film of the bioelectrode component is bonded to a biological surface, so that the needle part of the electrode member pierces the biological surface and is fixed thereto. When routine movement is performed with the bioelectrode component being fixed to the biological surface, the metal plate of the electrode member may float and move from the biological surface.

According to the bioelectrode component, since the needle part of the electrode member is coupled to the inner wall of the opening of the metal plate via the coupling bar, stress that is applied to the needle part due to the movement of the metal plate is relieved by the coupling bar.

Thereby, the needle part of the electrode member of the bioelectrode component is prevented from separating from the biological surface, so that it is possible to stably keep the state in which the needle part pierces the biological surface.

BRIEF DESCRIPTION OF THE DRAWINGS

FIG. 14 is a perspective view depicting the bioelectrode component of the second exemplary embodiment.

DETAILED DESCRIPTION

Hereinafter, exemplary embodiments will be described with reference to the accompanying drawings.

First Exemplary Embodiment

Figure 1:
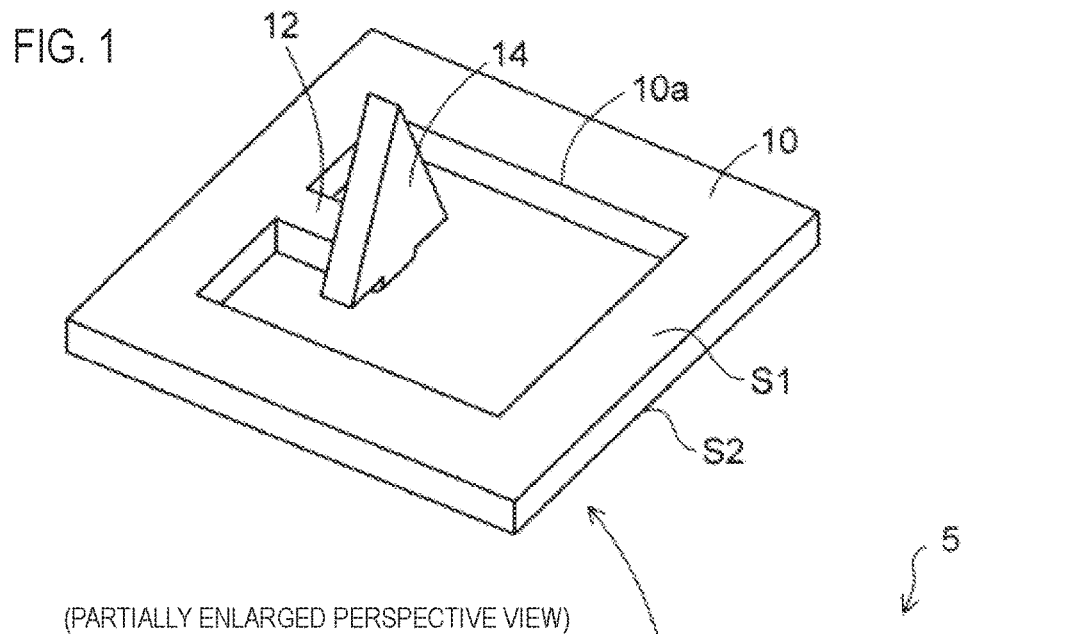
FIG. 1 is a perspective view depicting an electrode member of a bioelectrode component of a first exemplary embodiment.
Figure 1:
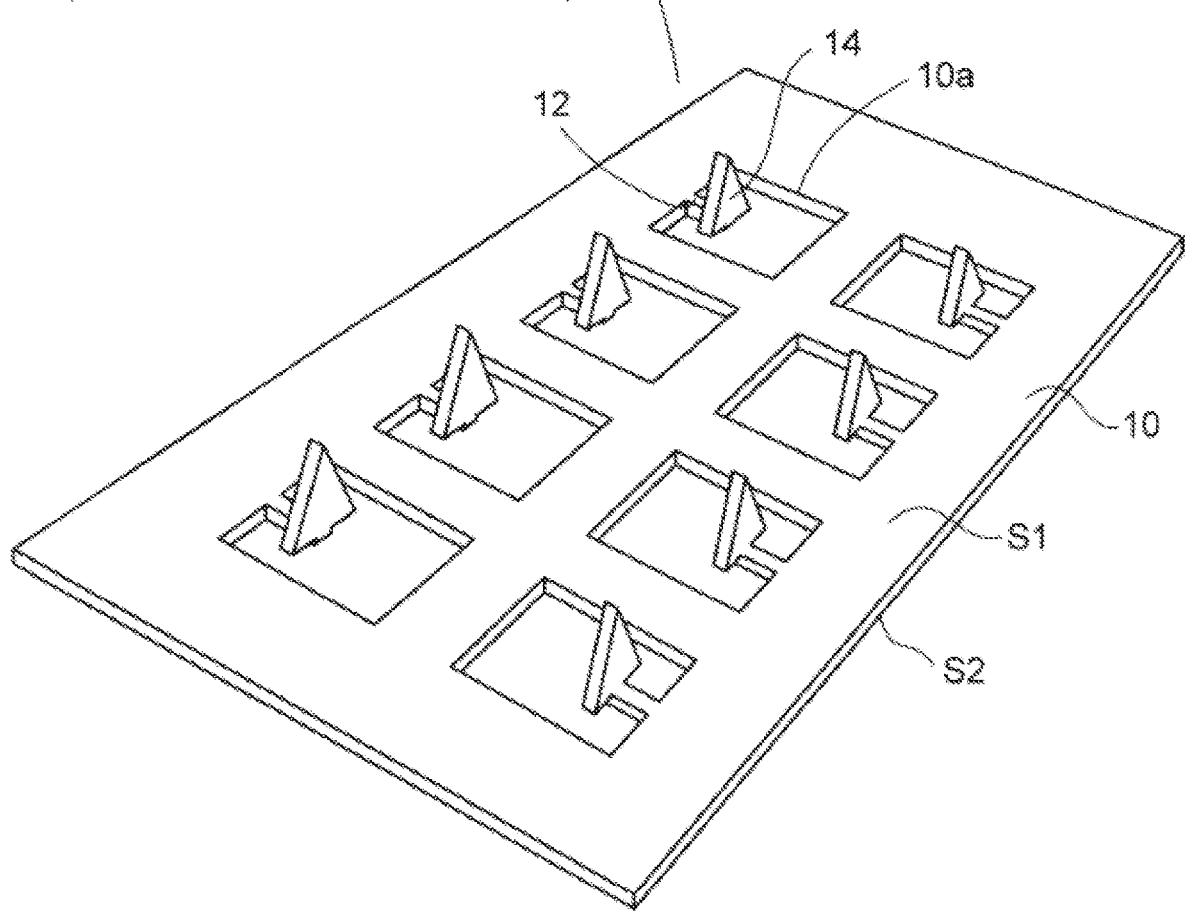

FIG. 1 is a perspective view depicting an electrode member of a bioelectrode component of a first exemplary embodiment. As shown in FIG. 1, an electrode member 5 that is used for a bioelectrode component of the first exemplary embodiment includes a thin plate-shaped metal plate 10, and the metal plate 10 is formed with a plurality of openings 10a. The opening 10a of the metal plate 10 is formed to penetrate the metal plate 10 in a thickness direction.

The metal plate 10 has a first surface S1 and a second surface S2 opposite to the first surface. In the example of FIG. 1, the first surface S1 of the metal plate 10 is an upper surface, and the second surface S2 is a lower surface.

As the metal plate 10, a metal foil made of titanium (Ti), nickel silver (copper (Cu)/zinc (Zn)/nickel (Ni) alloy) or the like is used. A thickness of the metal plate 10 is 0.05 mm to 0.1 mm, for example.

Referring to a partially enlarged perspective view of FIG. 1, the electrode member 5 includes a coupling bar 12 extending inward from an inner wall of the opening 10a of the metal plate 10. The coupling bar 12 is formed as a part of the metal plate 10, and is coupled to the inner wall of the opening 10a.

Also, a needle part 14 protruding toward the first surface S1 (the upper surface) of the metal plate 10 is arranged at a leading end of the coupling bar 12. The needle part 14 is bent from the leading end of the coupling bar 12 toward the first surface S1 (the upper surface) of the metal plate 10. The needle part 14 is formed as a part of the metal plate 10, and is erected vertically with being coupled to the leading end of the coupling bar 12.

In this way, the needle parts 14 are respectively arranged in the plurality of openings 10a of the metal plate 10 with being supported by the coupling bars 12.

In the example of FIG. 1, as seen from a side, the needle part 14 has a triangular shape having a sharp leading end, and a width of a bottom side of the needle part 14 is set greater than a width of the coupling bar 12.

Figure 2A:
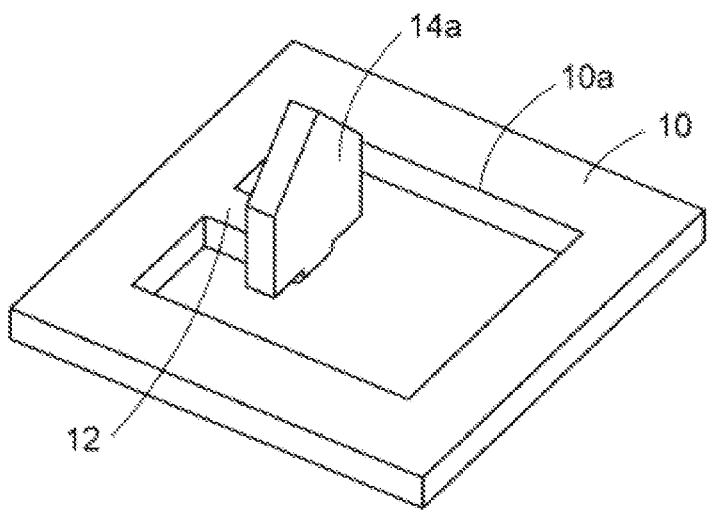
FIGS. 2A to 2C are perspective views depicting electrode members of bioelectrode components of modified embodiments of the first exemplary embodiment.

Alternatively, like a needle part 14a of a first modified embodiment shown in FIG. 2A, the needle part may have a pentagonal shape having a sharp leading end, as seen from a side.

Figure 2B:
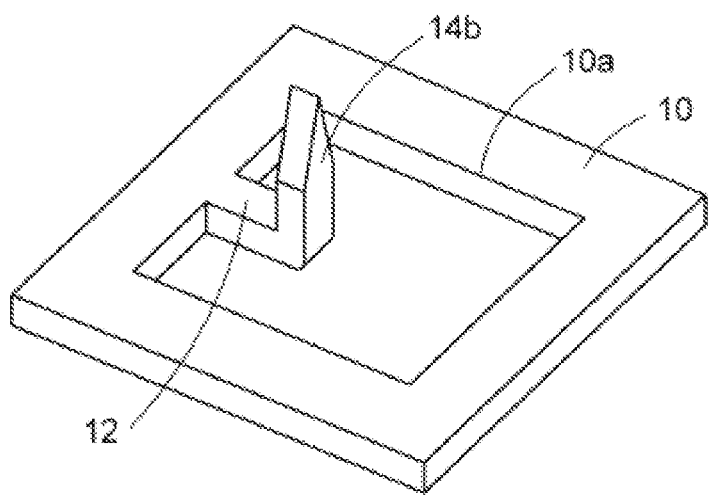

Also, like a needle part 14b of a second modified embodiment shown in FIG. 2B, a width of a base part of the needle part 14b may be set to be the same as the width of the coupling bar 12, as seen from a side.

Figure 2C:
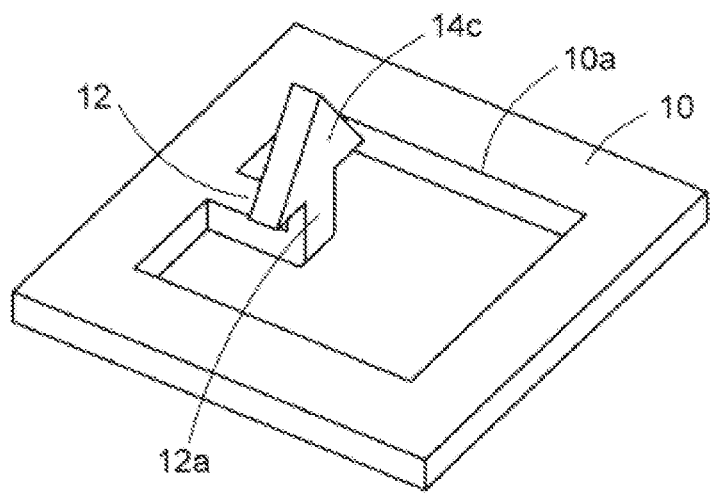

Also, like a needle part 14c of a third modified embodiment shown in FIG. 2C, a structure where a part of the leading end of the coupling bar 12 of the electrode member 5 shown in FIG. 1 is configured as an erection part 12a protruding toward the first surface S1 (the upper surface) of the metal plate 10 may be adopted. The erection part 12a of the coupling bar 12 is coupled to a central portion of the bottom surface of the needle part 14c.

As described later, an adhesive film of the bioelectrode component is bonded to a biological surface, so that the needle part 14 of the electrode member 5 pierces the biological surface and is fixed thereto. The coupling bar 12 of the electrode member 5 is provided so as to relieve stress, which is to be applied to the needle part 14 due to movement of the metal plate 10 of the electrode member 5, and to thus prevent the needle part 14 separating from the biological surface.

Since the needle part 14a of the first modified embodiment shown in FIG. 2A has a volume and a surface area greater than the needle part 14 of FIG. 1, a total area to contact the biological surface increases, so that it is possible to stably obtain information of a human body more correctly.

Also, since the width of the needle part 14b of the second modified embodiment shown in FIG. 2B is small, it is possible to reduce an arrangement pitch of the needle parts 14b, so that it is possible to configure the electrode member 5 having the needle parts 14b of a high density.

Also, in the example of the electrode member 5 shown in FIG. 1, the bottom surface of the triangular needle part 14 and the first surface S1 of the metal plate 10 (the upper surface of the coupling bar 12) are arranged at the same height position or at the close height positions. For this reason, when piercing the biological surface with the needle part 14 of the electrode member 5, the needle part 14 pierces the biological surface up to the position of the bottom surface thereof, and the bottom surface of the needle part 14 is exposed from the biological surface.

When adopting the needle part 14c of the third modified embodiment shown in FIG. 2C, since the needle part 14c pierces the biological surface up to the erection part 12a of the lower coupling bar 12, the bottom surface of the needle part 14 is embedded in the biological surface.

Therefore, since a part between the needle part 14c and the erection part 12a of the coupling bar 12 functions as an anchor, the needle part 14c can be prevented from separating from the biological surface.

Figure 3A:
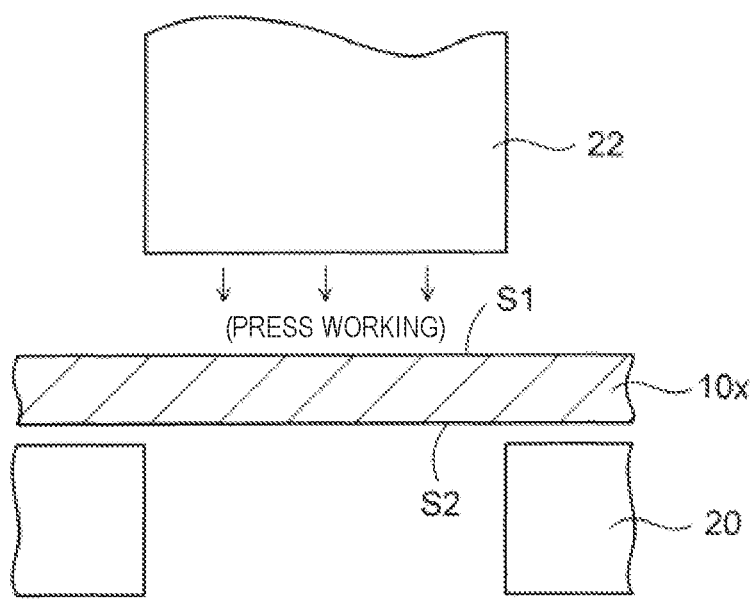
FIGS. 3A to 3C are sectional views and a perspective view depicting a manufacturing method of the electrode member of FIG. 1 (1 thereof).

Subsequently, a manufacturing method of the electrode member 5 of the bioelectrode component is described. As shown in FIG. 3A, a metal foil 10x having a thickness of 0.05 mm to 0.1 mm is first prepared. The metal foil 10x has the first surface S1 and the second surface S2 opposite to the first surface. The metal foil is an example of the metal plate. For the metal foil 10x, a plurality of product regions (not shown) for obtaining the electrode member is demarcated.

Then, the metal foil 10x is arranged on a die 20 of a mold, and the metal foil 10x is punched by a punch 22 of the mold.

Figure 3B:
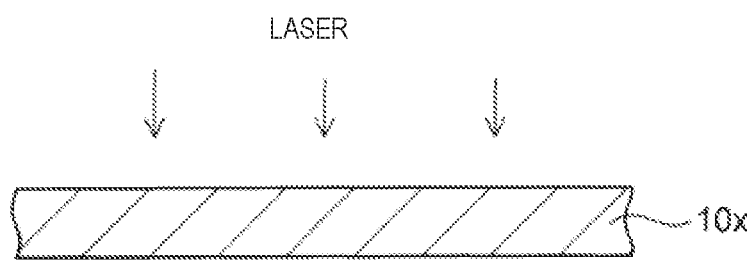

Alternatively, as shown in FIG. 3B, the metal foil 10x may be penetrated by laser, instead of the press working.

Figure 3C:
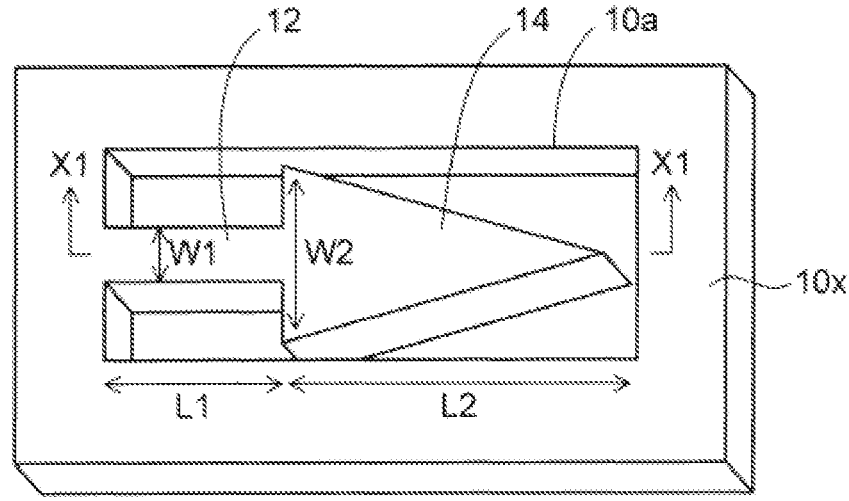

Thereby, as shown in FIG. 3C, the metal foil 10x is formed with the opening 10a. Also, at the same time, the coupling bar 12 extending inward from the inner wall of the opening 10a of the metal foil 10x and the needle part 14 coupled to the coupling bar 12 and having a triangular shape of which the leading end is sharp are formed. At this time, the needle part 14 is arranged with extending horizontally integrally with the coupling bar 12.

For example, a width W of the coupling bar 12 is set to 0.1 mm to 0.15 mm, and a length L1 is set to about 0.2 mm to 0.3 mm. Also, a width W2 of the bottom side of the needle part 14 is set to 0.15 mm to 0.2 mm and a length L2 is set to 0.2 mm to 0.3 mm.

Figure 4A:
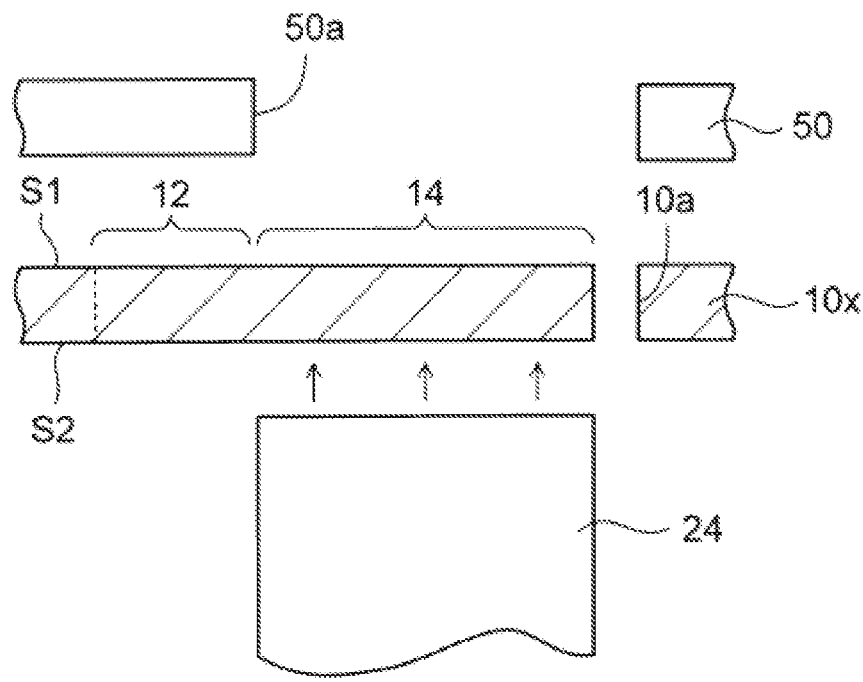
FIGS. 4A and 4B are a sectional view and a perspective view depicting the manufacturing method of the electrode member of FIG. 1 (2 thereof).

FIG. 4A depicts the metal foil 10x taken along a line X1-X1 of FIG. 3C. As shown in FIG. 4A, the needle part 14 arranged horizontally together with the coupling bar 12 in the opening 10a of the metal foil 10x is bent toward the first surface S1 (the upper surface) of the metal foil 10x by a punch 24 of the mold.

In a state where a die 50 having an opening 50a is arranged above the needle part 14 formed at the metal foil 10x, the needle part 14 is bent toward an upper side of the opening 50a by the punch 24.

Figure 4B:
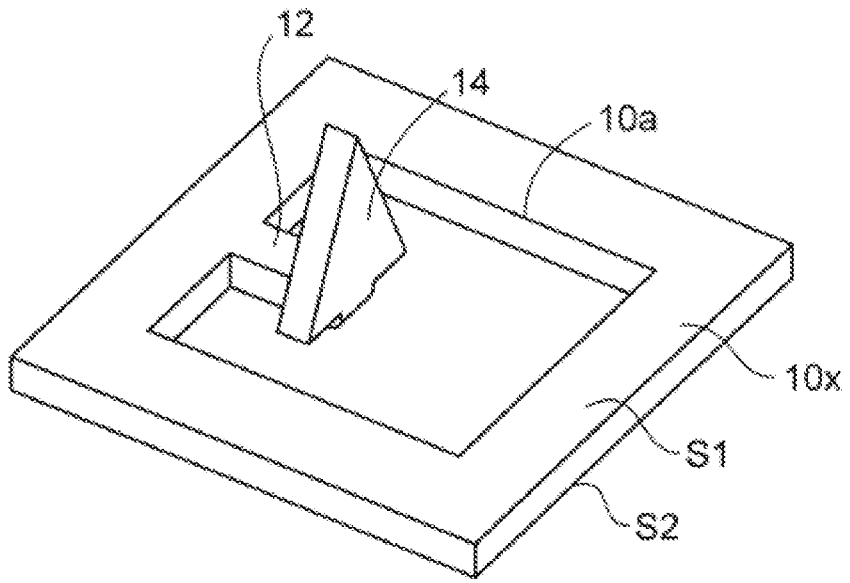

In this way, as shown in FIG. 4B, the needle part 14 is made to protrude from the leading end of the coupling bar 12 toward the first surface S1 (the upper surface) of the metal foil 10x. The needle part 14 is erected vertically from the leading end of the coupling bar 12 arranged horizontally.

Also, the metal foil 10x is cut so as to obtain each product region. By the above processes, the electrode member 5 of the bioelectrode component shown in FIG. 1 is manufactured.

When forming the needle part 14c of the third modified embodiment shown in FIG. 2C, during the press working of FIGS. 3C to 4B, a central part of the coupling bar 12 of FIG. 3C is bent toward the first surface S1 (the upper surface) so that the erection part 12a of the coupling bar 12 and the needle part 14c are to protrude.

Figure 5:
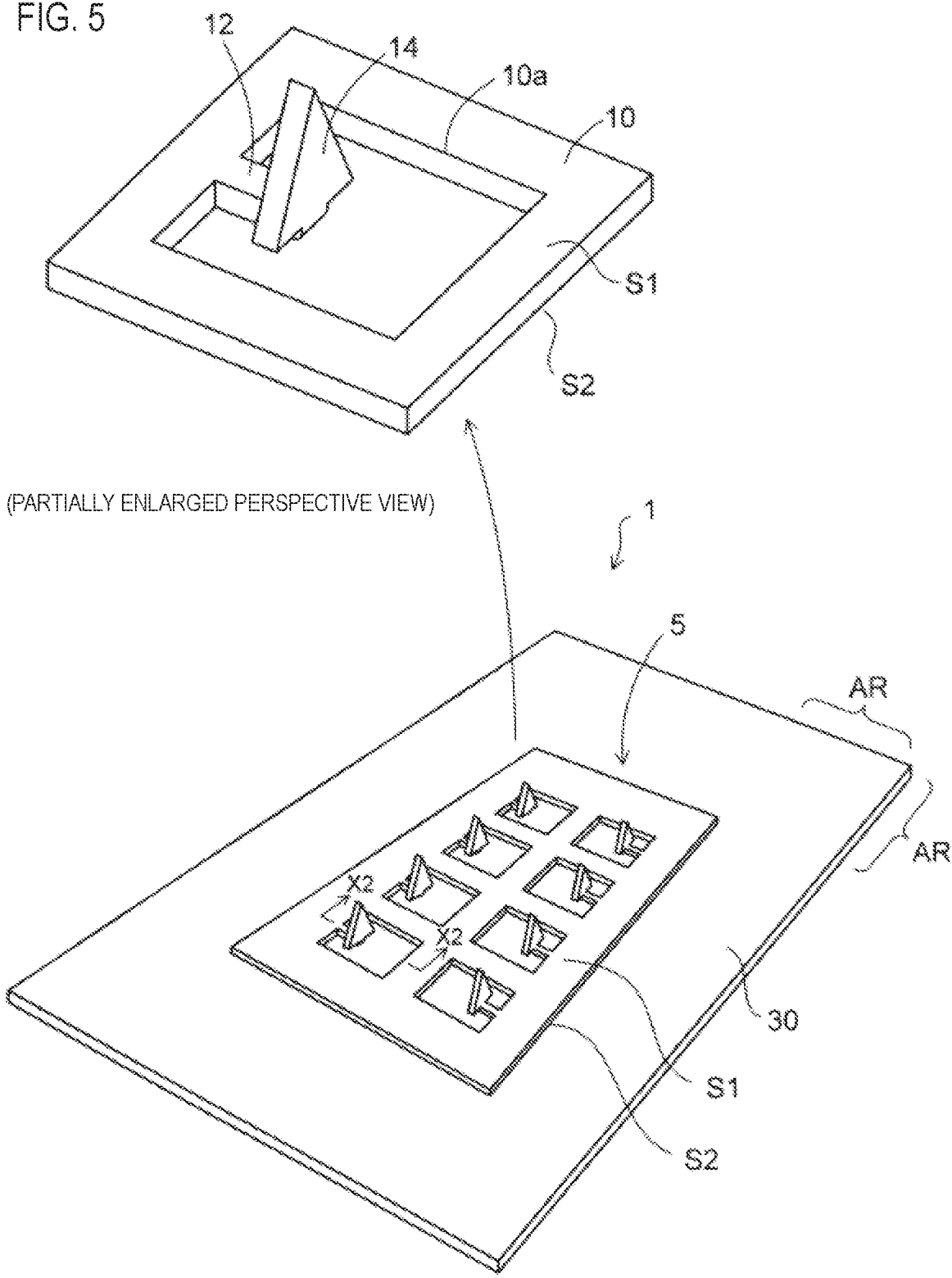
FIG. 5 is a perspective view depicting the bioelectrode component of the first exemplary embodiment.

FIG. 5 depicts a bioelectrode component 1 of the first exemplary embodiment for which the electrode member 5 of FIG. 1 is used. As shown in FIG. 5, the bioelectrode component 1 of the first exemplary embodiment includes the electrode member 5 of FIG. 1 and an adhesive film 30 bonded to the second surface S2 (the lower surface) of the metal plate 10 of the electrode member 5.

A size of the adhesive film 30 is set greater than a size of the electrode member 5, and the entire second surface S2 (the lower surface) of the metal plate 10 of the electrode member 5 is covered with the adhesive film 30. A peripheral edge region of the adhesive film 30 exposed from the electrode member 5 is configured as an adhesion region AR to be bonded to a biological surface.

The adhesive film 30 is bonded to the metal plate 10 of the electrode member 5 by an adhesive provided on its adhesion surface, and the adhesion region AR is also arranged thereon with the adhesive.

In this way, the adhesive film 30 has the ring-shaped adhesion region AR exposed from the electrode member 5 on a surface facing toward the first surface S1 (the upper surface) of the metal plate 10 of the electrode member 5.

In a state before the bioelectrode component 1 is fixed to the biological surface, the bioelectrode component 1 has a protection film (not shown) bonded to the electrode member 5 and the adhesion region AR of the adhesive film 30. The protection film is peeled off when bonding the bioelectrode component 1 to the biological surface.

The adhesion region AR of the adhesive film 30 is bonded to the biological surface, so that the needle part 14 of the electrode member 5 pierces the biological surface and is fixed thereto.

Figure 6A:
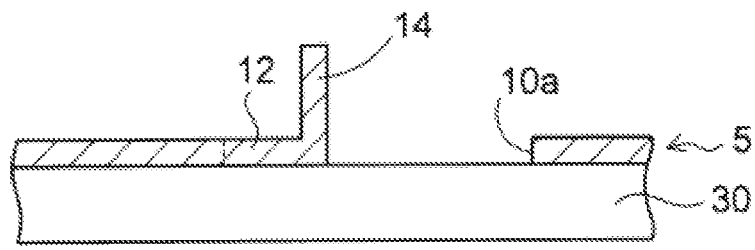
FIGS. 6A to 6C are sectional views depicting an aspect of fixing the bioelectrode component of the first exemplary embodiment to a biological surface.

Subsequently, a method of fixing the bioelectrode component 1 of the first exemplary embodiment to the biological surface is described. FIG. 6A is a partial sectional view taken along a line X2-X2 of the bioelectrode component 1 shown in FIG. 5, in which the coupling bar 12 and the needle part 14 arranged in one opening 10a of the metal plate 10 are partially shown.

Figure 6B:
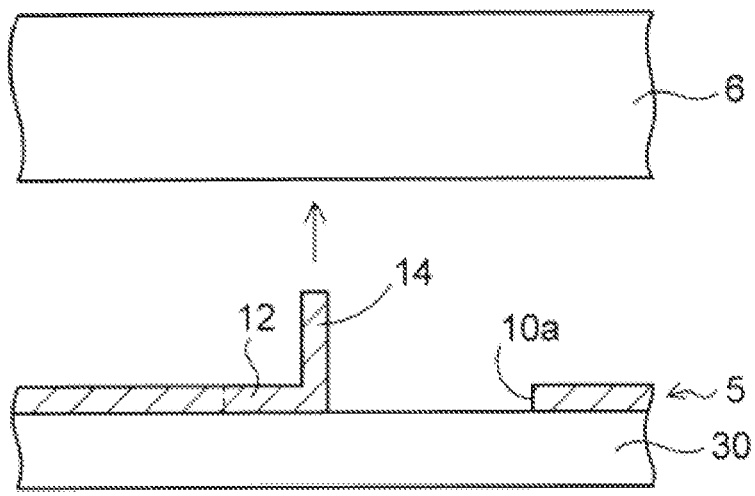
Figure 6C:
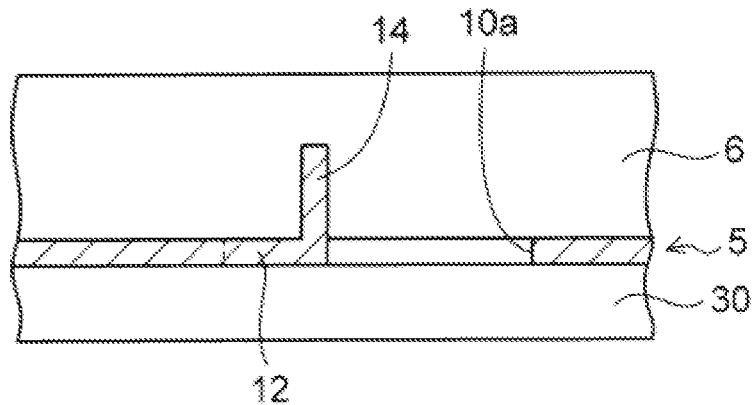

As shown in FIGS. 6B and 6C, a biological surface 6 is pierced with the needle part 14 of the electrode member 5 of the bioelectrode component. The biological surface 6 is skin, a mucous membrane or the like of the human body.

At this time, although not particularly shown, the adhesion region AR of the adhesive film 30 of the bioelectrode component 1 shown in FIG. 5 is bonded to the biological surface 6, and the electrode member 5 is pressed to the biological surface 6. Thereby, the electrode member 5 is fixed to the biological surface 6 by the adhesive film 30 with the plurality of needle parts 14 of the electrode member 5 piercing the biological surface 6 at the same time.

When measuring a variety of biosignals by the bioelectrode component 1, the electrode member 5 is connected to a measurement device by an electric wire (not shown). Alternatively, a medicinal agent such as vaccine arranged in the electrode member 5 may be medicated into the biological surface for a predetermined time period.

At this time, when routine movement is performed with the bioelectrode component 1 being fixed to the biological surface 6, the metal plate 10 of the electrode member 5 may float and move from the biological surface 6.

According to the electrode member 6 of the bioelectrode component 1 of the first exemplary embodiment, since the needle part 14 is coupled to the inner wall of the opening 10a of the metal plate 1 via the coupling bar 12, the stress that is applied to the needle part 14 due to the movement of the metal plate 10 is relieved by the coupling bar 12.

When the metal plate 10 of the electrode member 5 moves in each direction, the coupling bar 12 configured to support the needle part 14 is bent, so that the movement of the metal plate 10 is not directly transmitted to the needle part 14. Accordingly, the stress that is applied to the needle part 14 is relieved.

Thereby, the needle part 14 of the bioelectrode component 1 is prevented from separating from the biological surface 6, so that it is possible to stably keep the piercing state of the needle part 14 in the biological surface 6.

Unlike the first exemplary embodiment, in a structure where the base part of the needle part is directly coupled to the inner wall of the opening of the metal plate, since the movement of the metal plate is directly transmitted to the needle part, the needle part is likely to separate from the biological surface, in conformity to the movement of the metal plate.

Here, in FIG. 6C, the lower surfaces of the coupling bar 12 and the needle part 14 of the electrode member 5 are bonded to the adhesive film 30. For this reason, when the routine movement is performed with the bioelectrode component 1 being fixed to the biological surface 6, the needle part 14 coupled to the coupling bar 12 may be likely to separate from the biological surface 6, in association with the movement of the adhesive film 30.

Figure 7A:
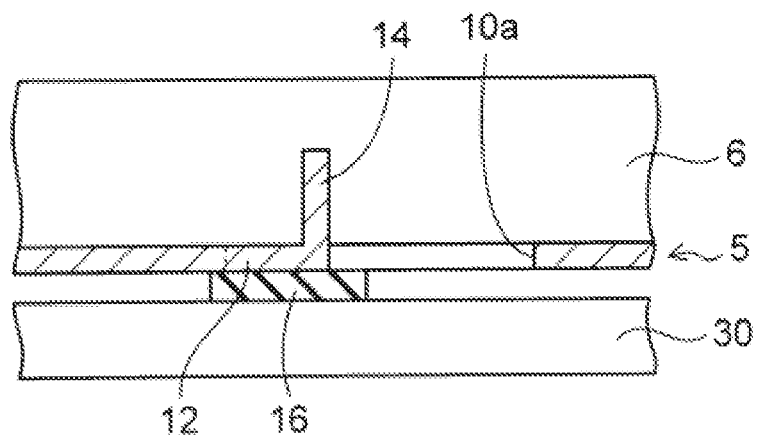
FIGS. 7A and 7B are sectional views depicting an aspect of fixing a bioelectrode component of a modified embodiment of the first exemplary embodiment to the biological surface.

For this reason, as shown in FIG. 7A, a cover member 16 may be arranged between the coupling bar 12 and needle part 14 and the adhesive film 30. The cover member 16 is made of a cured resin layer, for example, and is obtained by patterning a silicone resin or the like on the adhesion surface of the adhesive film 30. The adhesive film 30 having the cover member 16 formed on the adhesion surface is positionally aligned and bonded to the electrode member 5.

A lower surface of the cover member 16 is bonded to the adhesive film 30, and an upper surface and side surfaces of the cover member 16 have no adhesiveness.

For this reason, the coupling bar 12 and the needle part 14 are just in contact with the cover member 16. Therefore, even when the adhesive film 30 moves, the cover member 16 bonded to the adhesive film 30 is separated from the coupling bar 12 and the needle part 14. Therefore, the separation of the needle part 14 from the biological surface 6 in association with the movement of the adhesive film 30 is prevented.

In FIG. 7A, the cover member 16 is respectively arranged in an island shape on the adhesive film 30 of parts corresponding to the coupling bar 12 and the needle part 14 in each opening 10a of the metal plate 10. In addition, like a modified embodiment of FIG. 7B, the cover member 16 greater than the opening 10a may be individually arranged below each opening 10a of the metal plate 10.

Figure 8:
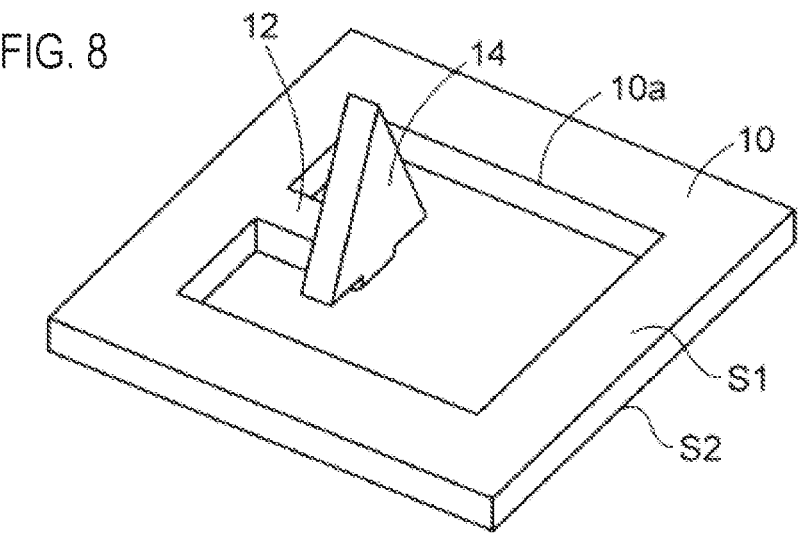
FIG. 8 is a perspective view depicting a bioelectrode component of another modified embodiment of the first exemplary embodiment.
Figure 8:
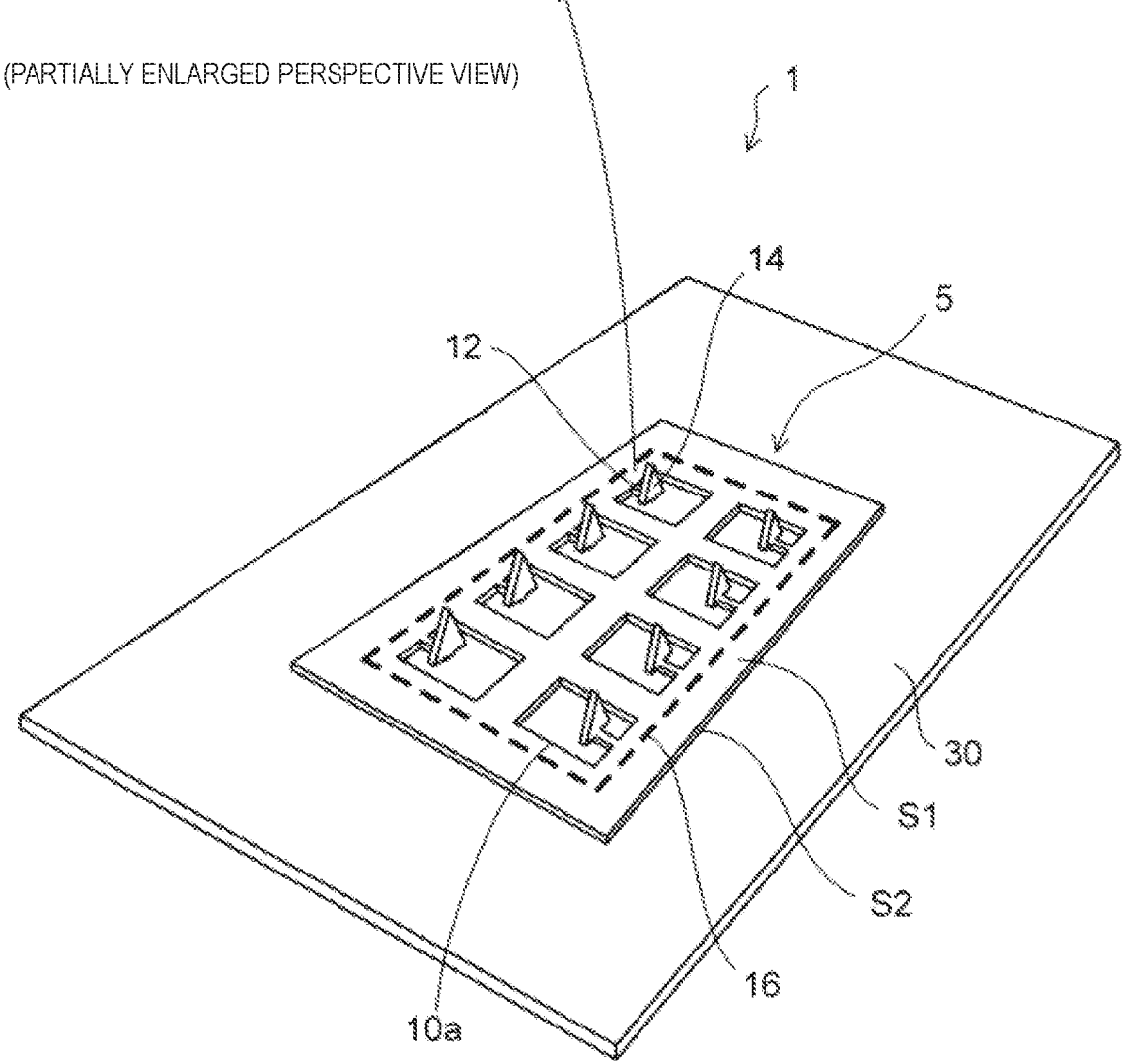

Alternatively, like another modified embodiment of FIG. 8, the cover member 16 may be collectively arranged in a region (a region surrounded by the thick dotted line) greater than a collective region in which the plurality of openings 10a of the metal plate 10 is arranged. In this case, only a peripheral edge part of the metal plate 10 around the cover member 16 is bonded to the adhesive film 30.

Like this, the cover member 16 is preferably arranged so that the coupling bar 12 and needle part 14 of the electrode member 5 and the adhesive film 30 are not to be bonded.

Figure 9A:
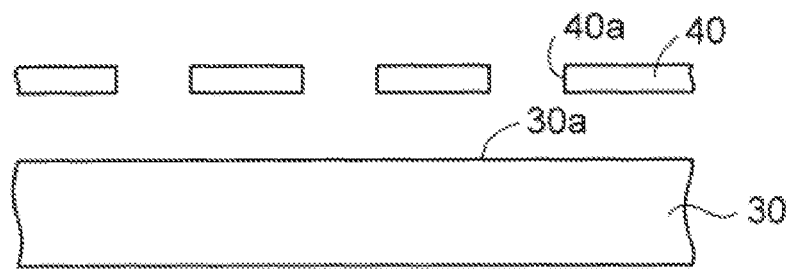
FIGS. 9A to 9C are sectional views depicting a method of forming a cover member on an adhesive film (1 thereof).

In the below, a method of forming the cover member 16 on the adhesive film 30 is described. As shown in FIG. 9A, the adhesive film 30 is first prepared, and an adhesion surface 30a of the adhesive film 30 on which an adhesive is arranged is made to face upward.

Subsequently, a mask layer 40 having openings 40a formed in regions in which the cover members 16 are to be arranged is prepared. The mask layer 40 is formed as a release film of which a peeling surface is applied with a release agent and can be thus easily peeled off after being temporarily bonded to the adhesion surface 30a of the adhesive film 30.

Figure 9B:
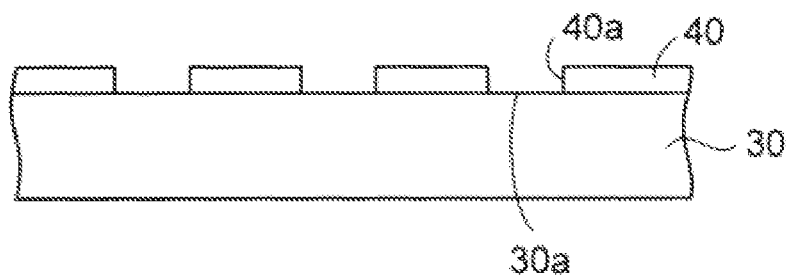

Then, as shown in FIG. 9B, the mask layer 40 is temporarily bonded to the adhesion surface 30a of the adhesive film 30.

Figure 9C:
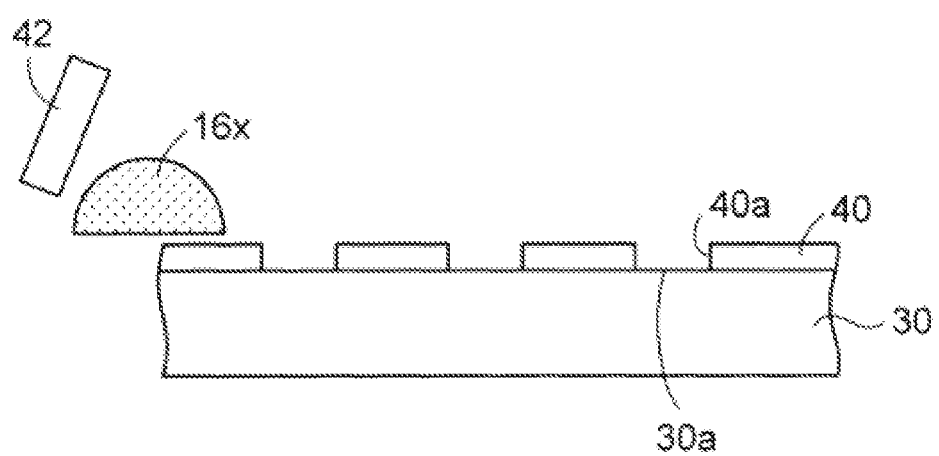
Figure 10A:
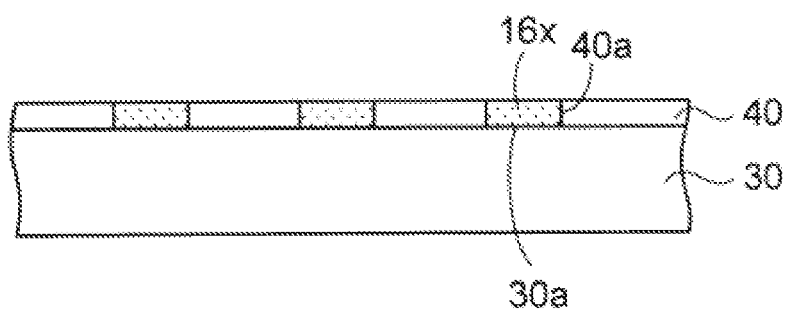
FIGS. 10A and 10B are sectional views depicting the method of forming the cover member on the adhesive film (2 thereof).

Also, as shown in FIG. 9C, a resin material 16x of liquid phase or paste phase is arranged above the mask layer 40, and the resin material 16x is laterally moved by a squeegee 42. Thereby, as shown in FIG. 10A, the resin material 16x is patterned and formed on the adhesive film 30 through the openings 40a of the mask layer 40.

Figure 10B:
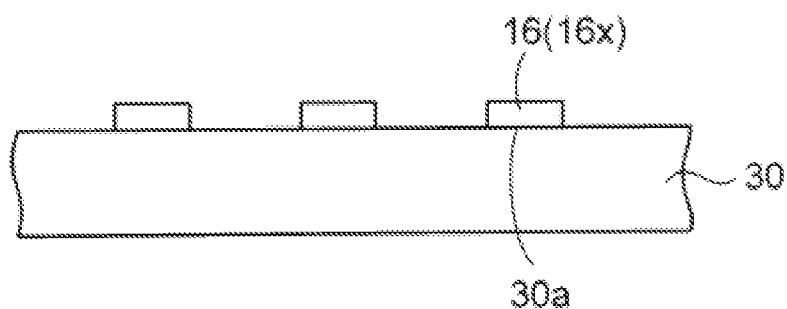

Subsequently, as shown in FIG. 10B, the mask layer 40 is detached and removed from the structure of FIG. 10A. Since the mask layer 40 is made of the release film, the mask layer can be peeled off without deteriorating the adhesion surface 30a of the adhesive film 30.

Also, before or after peeling off the mask layer 40, the resin material 16x is heated and cured, so that the cover members 16 are obtained.

As another method of forming the cover member 16, a resin film cut into a predetermined size may be bonded to the adhesion surface 30a of the adhesive film 30. Alternatively, the resin material may be applied in a pattern shape on the adhesion surface 30a of the adhesive film 30 by an inkjet or dispenser.

In the above, the cover member 16 is formed of the resin. However, a member of which a surface has no adhesiveness may be arranged on the adhesion surface of the adhesive film 30, and a metal layer or the like may also be used.

Like this, according to the bioelectrode component 1 of the first exemplary embodiment, it is possible to stably keep the state in which the biological surface 6 is pierced with the small needle parts 14. For this reason, it is possible to correctly measure the biosignals such as electrocardiogram, brain wave, electromyogram and the like. Also, it is possible to reliably medicate the medicinal agent such as vaccine into the biological body for a predetermined time period.

Second Exemplary Embodiment

Figure 11:
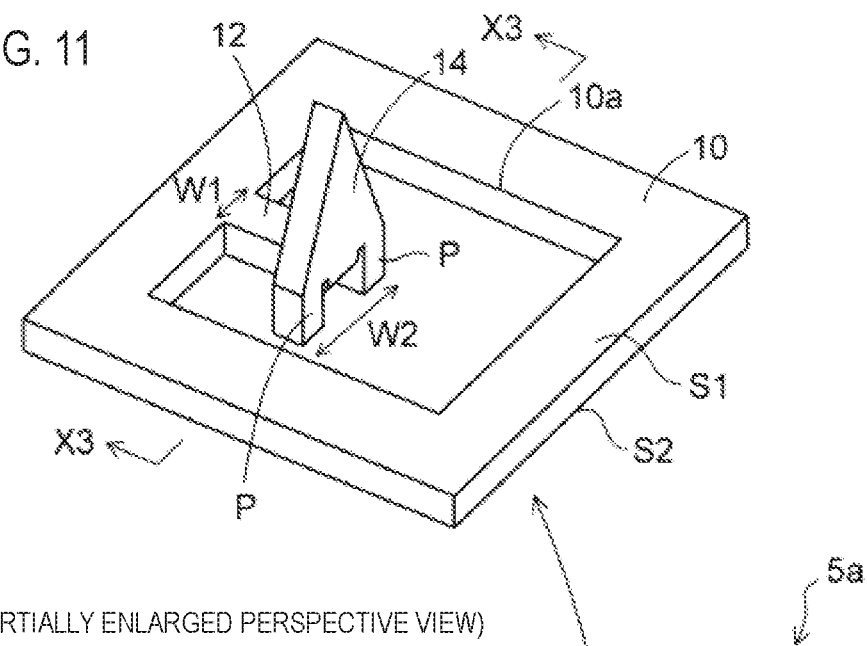
FIG. 11 is a perspective view depicting an electrode member of a bioelectrode component of a second exemplary embodiment.
Figure 11:
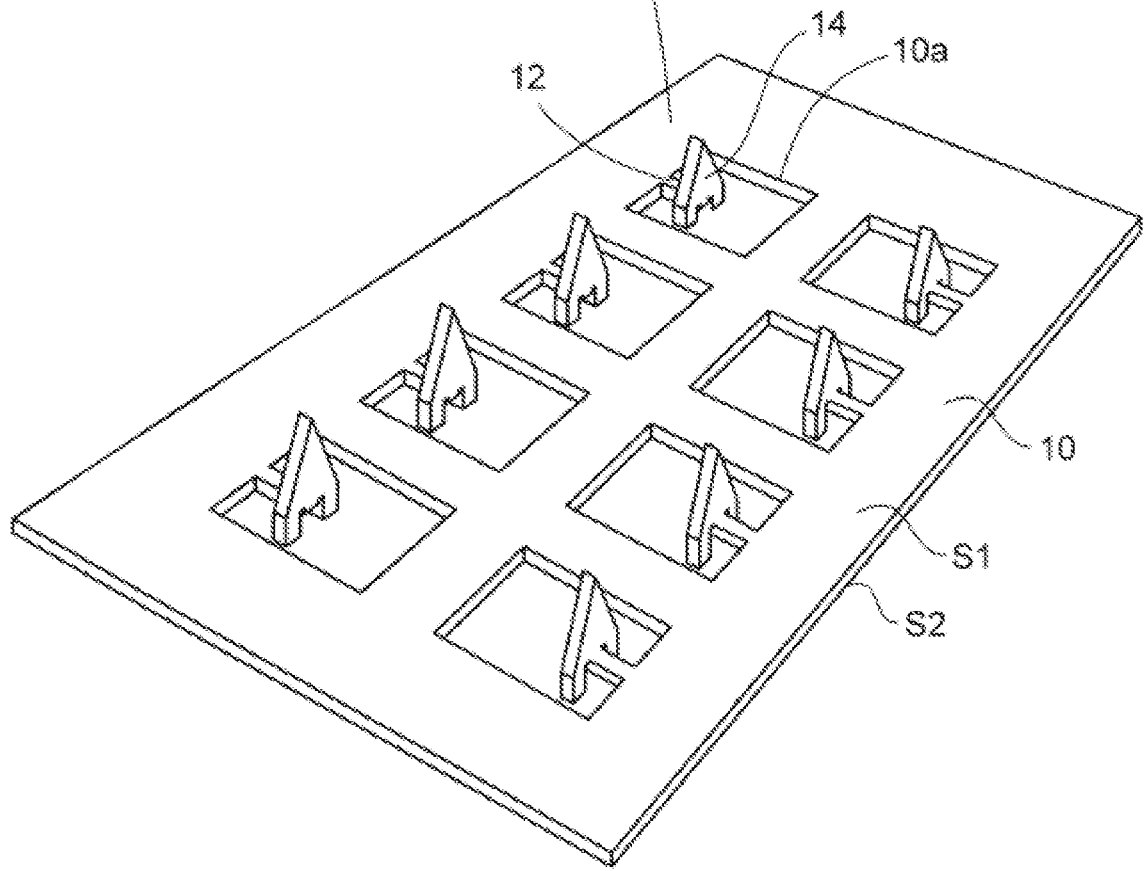

FIG. 11 is a perspective view depicting an electrode member of a bioelectrode component of a second exemplary embodiment. As shown in FIG. 11, an electrode member 5a that is used for the bioelectrode component of the second exemplary embodiment is different from the electrode member 5 of the first exemplary embodiment shown in FIG. 1, in terms of the shape of the needle part 14.

As shown in a partially enlarged perspective view of FIG. 11, the width W2 of the needle part 14 is set greater than the width W1 of the coupling bar 12. The needle part 14 has protrusions P protruding toward the second surface S2 (the lower surface) of the metal plate 10 at both end portions in the width W2 direction.

Figure 12:
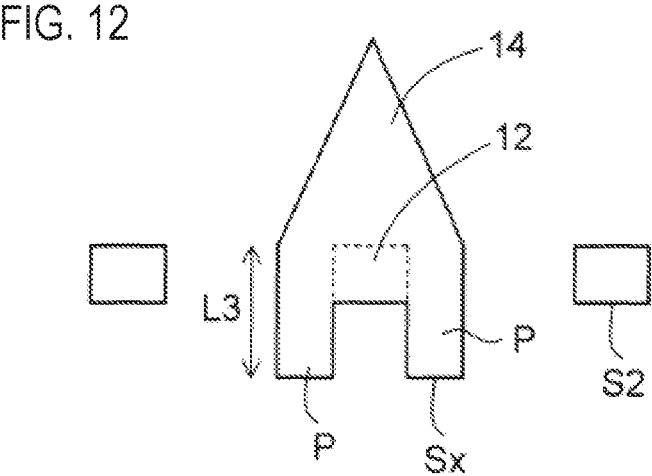
FIG. 12 is a sectional view taken along a line X3-X3 of the electrode member shown in FIG. 11.

FIG. 12 is a sectional view taken along a line X3-X3 of the partially enlarged perspective view of FIG. 11. Referring to FIG. 12, the needle part 14 has a shape where a triangular shape having a sharp leading end and two rectangular protrusions P formed at both end portions of a bottom surface of the triangular shape are combined each other, as seen from a side.

The two protrusions P formed at the lower part of the needle part 14 protrude to an outermore position than the second surface S2 (the lower surface) of the metal plate 10, and lower end faces Sx of the protrusions P are arranged at a lower position than the second surface S2 (the lower surface) of the metal plate 10.

For example, when a thickness of the metal plate 10 is 0.1 mm, a protruding length L3 of the protrusion P is set to about 0.2 mm, and the lower end face Sx of the protrusion P protrudes by about 0.1 mm from the second surface S2 (the lower surface) of the metal plate 10.

As described later, when piercing the biological surface with the needle part 14 of the electrode member 5a, if the protrusions P of the needle part 14 are pushed, the coupling bar 12 is moved obliquely upward, so that the needle part 14 pierces the biological surface at an obliquely inclined state. Thereby, the needle part 14 is difficult to separate from the biological surface.

Figure 13A:
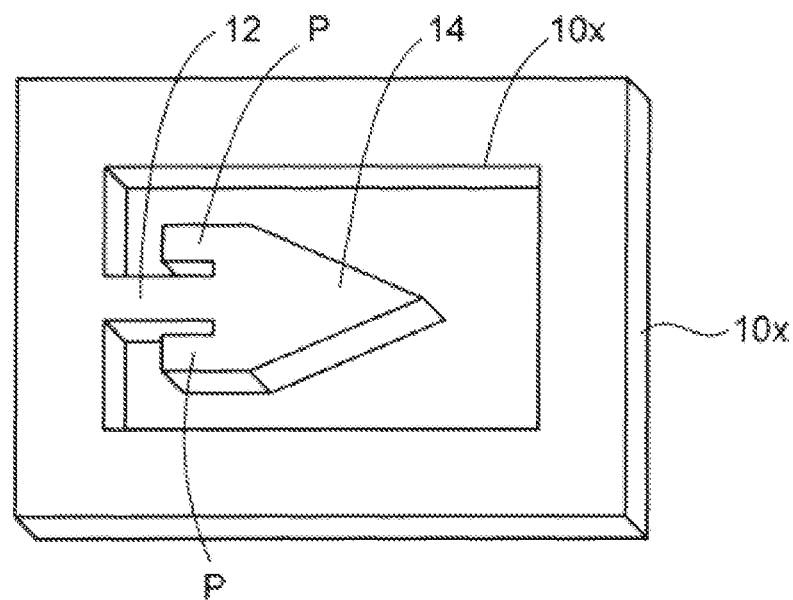
FIGS. 13A and 13B are perspective views depicting a manufacturing method of the electrode member of FIG. 11.

Subsequently, a method of manufacturing the electrode member 5a of the bioelectrode component of the second exemplary embodiment shown in FIG. 11 is described. As shown in FIG. 13A, the metal foil 10x is punched in the similar method to the process of FIG. 3A by the press working, so that the metal foil 10x is formed with the opening 10a. At the same time, the coupling bar 12 extending inward from the inner wall of the opening 10a of the metal foil 10x and the needle part 14 coupled to the coupling bar 12 are integrally arranged in the horizontal direction.

The needle part 14 is coupled to the coupling bar 12, and has the triangular part having a sharp leading end and the two protrusions P extending from both end portions of the bottom surface of the triangular part toward the inner wall of the opening 10a. The protrusions P of the needle part 14 are arranged in regions between the coupling bar 12 and the inner walls of the opening 10a.

Alternatively, the metal foil 10x may be perforated by the laser, so that the pattern as shown in FIG. 13A may be formed on the metal foil 10x.

Figure 13B:
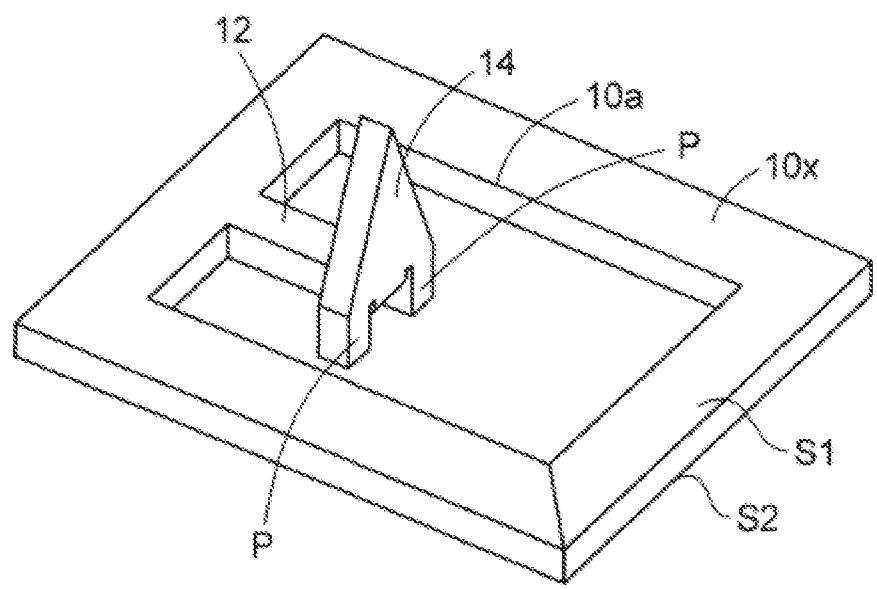

Then, as shown in FIG. 13B, the triangular part of the needle part 14 of FIG. 13A is bent toward the first surface S1 (the upper surface) of the metal foil 10x in the similar manner to the processes of FIGS. 4A and 4B by a punch (not shown).

In this way, the triangular part of the needle part 14 is made to protrude toward the first surface S1 (the upper surface) of the metal foil 10x, and the protrusions P of the needle part 14 are made to protrude toward the second surface S1 (the lower surface) of the metal foil 10x. By the above processes, the electrode member 5a of FIG. 11 is manufactured.

FIG. 14 depicts a bioelectrode component 1a of the second exemplary embodiment for which the electrode member 5a of FIG. 11 is used. As shown in FIG. 14, like the first exemplary embodiment of FIG. 5, the adhesive film 30 is bonded to the second surface S2 of the metal plate 10 of the electrode member 5a, so that the bioelectrode component 1a of the second exemplary embodiment is configured.

In FIG. 14, the bioelectrode component 1a is the same as the bioelectrode component 1 of the first exemplary embodiment shown in FIG. 5, except that the needle part 14 of the electrode member 5a has the protrusions P at the lower side thereof.

Figure 15A:
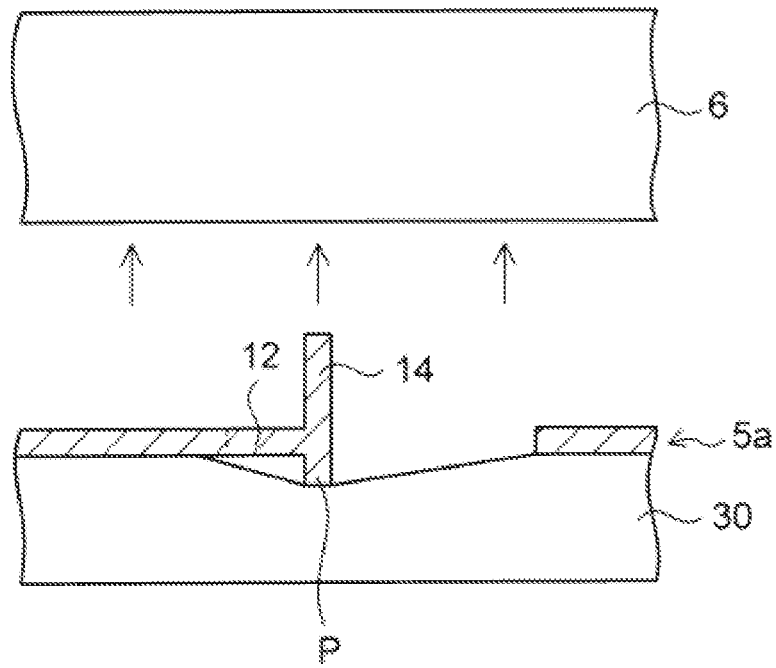
FIGS. 15A and 15B are sectional views depicting an aspect of fixing the bioelectrode component of the second exemplary embodiment to the biological surface.

Subsequently, a method of fixing the bioelectrode component 1a of the second exemplary embodiment of FIG. 14 to the biological surface is described. FIG. 15A is a sectional view taken along a line X4-X4 of the bioelectrode component 1a of FIG. 14, in which the coupling bar 12 and the needle part 14 arranged in one opening 10a of the metal plate 10 are partially shown.

As shown in FIG. 15A, like FIGS. 6B and 6C, the adhesion region AR of the adhesive film 30 of the bioelectrode component 1a of FIG. 14 is bonded to the biological surface 6 and the electrode member 5a is pressed to the biological surface 6, so that the biological surface 6 is pierced with the needle part 14.

Figure 15B:
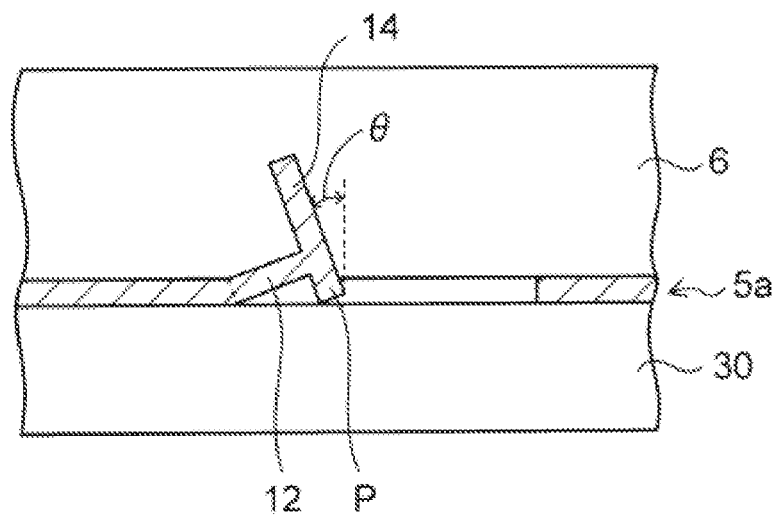

At this time, according to the bioelectrode component of the second exemplary embodiment, the needle part 14 has the protrusions P provided at the lower part thereof and protruding to the position lower than the lower surface of the metal plate 10. For this reason, as shown in FIG. 15B, when piercing the biological surface 6 with the needle part 14, the protrusions P of the needle part 14 are pressed to the biological surface 6 via the adhesive film 30.

Accompanied by this, the coupling bar 12 coupled to the needle part 14 is moved obliquely upward, so that the needle part 14 pierces the biological surface 6 at an obliquely inclined state.

Thereby, as compared to a case where the needle part 14 pierces vertically the biological surface 6, the needle part 14 is more difficult to separate from the biological surface 6. An inclination angle θ relative to a vertical axis of the needle part 14 is set within a range of 10° to 30°, and is preferably set to 200.

Also, when the protrusions P of the needle parts 14 are pushed into the biological surface 6, the biological surface 6 can be uniformly and securely pierced up to a predetermined depth with the plurality of needle parts 14.

Here, in FIGS. 15A and 15B, when piercing the biological surface 6 with the needle part 14, if the hardness of the adhesive film 30 is low, the protrusions P of the needle part 14 may be inserted into the adhesive film 30 without being sufficiently pressed toward the biological surface 6. In this case, since the needle part 14 is inserted vertically into the biological surface 6 without being inclined, the sufficient separation preventing effect is not obtained.

Figure 16A:
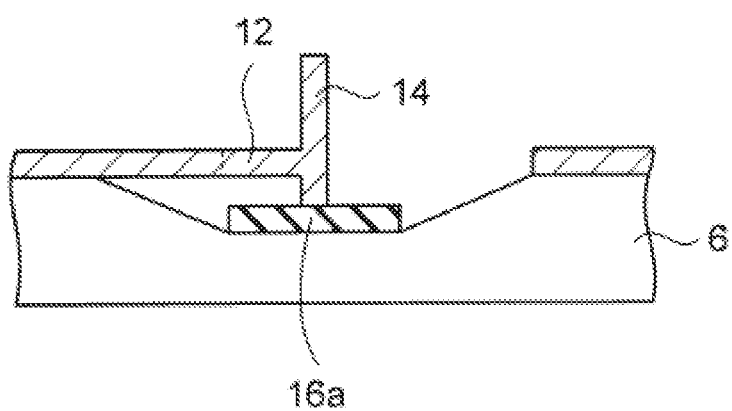
FIGS. 16A and 16B are sectional views depicting an aspect of fixing a bioelectrode component of a modified embodiment of the second exemplary embodiment to the biological surface.

For this reason, as shown in FIG. 16A, a cover member 16a may be arranged between the protrusions P of the needle part 14 of FIG. 15A and the adhesive film 30. The cover member 16a shown in FIG. 16A is formed on the adhesion surface of the adhesive film 30 in the similar direction to the formation method of FIGS. 9A to 10B. The cover member 16a is preferably formed of a cured resin layer. However, a metal layer or the like may also be used.

Figure 16B:
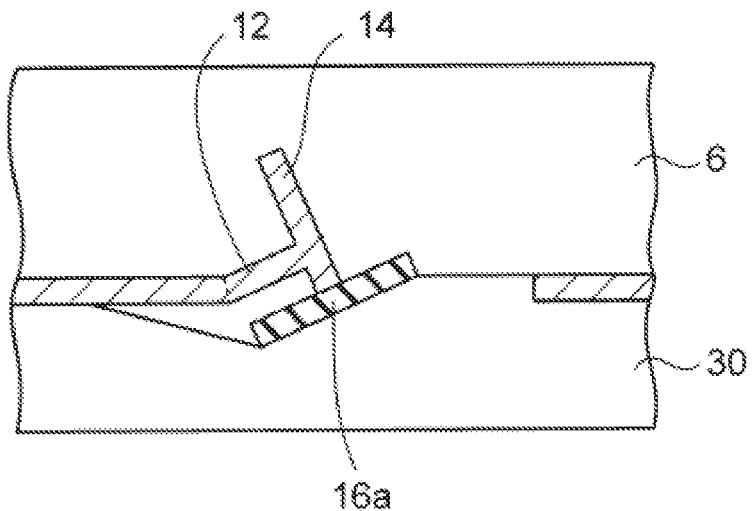

As shown in FIG. 16B, the needle part 14 of the electrode member 5a is enabled to pierce the biological surface 6 with being pressed thereto. At this time, since the rigid cover member 16a is arranged below the protrusions P of the needle part 14, the protrusions P of the needle part 14 are securely pressed to the biological surface 6 by the cover member 16a.

Therefore, since there is no probability that the protrusions P of the needle part 14 will be inserted into the adhesive film 30, it is possible to securely pierce the biological surface 6 with the needle part 14 at the inclined state.

Also, like the first exemplary embodiment, since the protrusions P of the needle part 14 and the adhesive film 30 are separated by the cover member 16a, the separation of the needle part 14 due to the movement of the adhesive film 30 is prevented.

Also, in FIG. 16A, like the modified embodiment of FIG. 7A, the cover member 16a is respectively arranged in an island shape at a part corresponding to the protrusion P of the needle part 14 in each opening 10a of the metal plate 10.

Figure 7B:
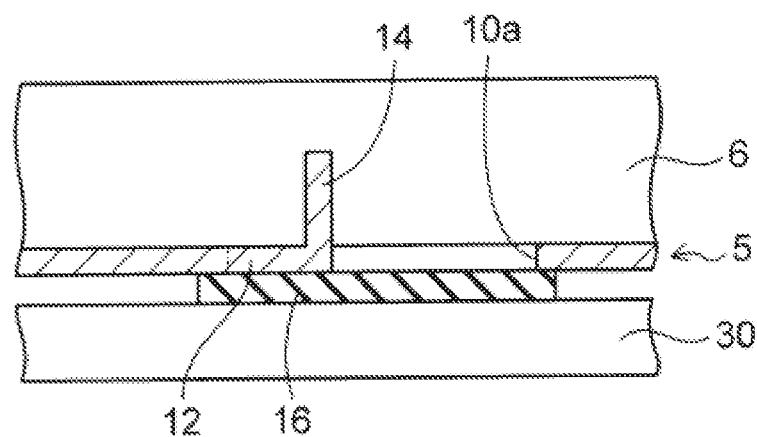

In addition, like the modified embodiment of FIG. 7B, the cover member 16a greater than the opening 10a may be individually arranged below each opening 10a of the metal plate 10.

Alternatively, like the modified embodiment of FIG. 8, the cover member 16a may be collectively arranged in a region (a region surrounded by the thick dotted line) greater than the collective region in which the plurality of openings 10a of the metal plate 10 is arranged.

This disclosure further encompasses various exemplary embodiments, for example, described below.

1. A manufacturing method of a bioelectrode component, the manufacturing method comprising:

processing a metal plate having a first surface and a second surface opposite to the first surface to form an opening, a coupling bar extending inward from an inner wall of the opening and a needle part coupled to the coupling bar; and bending the needle part so as to protrude toward the first surface of the metal plate, thereby obtaining an electrode member.

2. The manufacturing method of a bioelectrode component according to claim 1, wherein in the obtaining the electrode member, a width of the needle part is set greater than a width of the coupling bar, and the needle part is formed to have protrusions provided at both end portions thereof and protruding toward the second surface of the metal plate.

3. The manufacturing method of a bioelectrode component according to claim 1 or 2, further comprising:

bonding an adhesive film to the second surface of the metal plate of the electrode member, after the obtaining the electrode member, wherein the adhesive film has an adhesion region, which is exposed from the electrode member, on a surface facing toward the first surface of the metal plate.

4. The manufacturing method of a bioelectrode component according to claim 3, wherein in the bonding the adhesive film, a cover member is arranged between the coupling bar and needle part of the electrode member and the adhesive film.

What is claimed is:

1. A bioelectrode component comprising:
an electrode member, the electrode member comprising:
a metal plate including a first surface and a second surface opposite to the first surface and including an opening formed in the metal plate,
a coupling bar extending inward from an inner wall of the opening, and
a needle part arranged at a leading end of the coupling bar and protruding toward the first surface of the metal plate,
wherein a width of the needle part is set greater than a width of the coupling bar, and
wherein the needle part has protrusions provided at both end portions thereof and protruding toward the second surface of the metal plate.

2. The bioelectrode component according to claim 1, wherein the needle part has a triangular or pentagonal shape of which a leading end is sharp, as seen from a side.

3. The bioelectrode component according to claim 2, wherein the protrusions protrude from a trailing end of the needle part and protrude beyond the coupling bar toward the second surface of the metal plate.

4. The bioelectrode component according to claim 3, wherein the needle part protrudes from the first surface of the metal plate.

5. The bioelectrode component according to claim 4, wherein the coupling bar extends in parallel with the first surface of the metal plate.

6. The bioelectrode component according to claim 1, further comprising:
an adhesive film bonded to the second surface of the metal plate of the electrode member,
wherein the adhesive film has an adhesion region, which is exposed from the electrode member, on a surface facing toward the first surface of the metal plate.

7. The bioelectrode component according to claim 6, further comprising:
a cover member arranged between the coupling bar and needle part of the electrode member, and the adhesive film.

8. The bioelectrode component according to claim 6, wherein the adhesion region of the adhesive film is adapted to be bonded to a biological surface, so that the needle part of the electrode member is enabled to pierce the biological surface and is fixed thereto.

9. The bioelectrode component according to claim 1, wherein the coupling bar extends in parallel with the first surface of the metal plate.

10. The bioelectrode component according to claim 9, wherein the protrusions protrude beyond the coupling bar toward the second surface of the metal plate.

11. The bioelectrode component according to claim 10, wherein the needle part protrudes from the first surface of the metal plate.

12. The bioelectrode component according to claim 1, wherein the protrusions protrude beyond the coupling bar toward the second surface of the metal plate.

13. The bioelectrode component according to claim 12, wherein the needle part protrudes from the first surface of the metal plate.

14. The bioelectrode component according to claim 13, wherein the protrusions are provided at both end portions of the needle part in a width direction.

15. The bioelectrode component according to claim 12, wherein the protrusions are provided at both end portions of the needle part in a width direction.

16. The bioelectrode component according to claim 15, wherein the coupling bar extends in parallel with the first surface of the metal plate.

17. The bioelectrode component according to claim 16, wherein the needle part protrudes from the first surface of the metal plate.

18. The bioelectrode component according to claim 1, wherein the protrusions are provided at both end portions of the needle part in a width direction.

19. The bioelectrode component according to claim 1, wherein the needle part protrudes from the first surface of the metal plate.

* * * * *